United States Patent [19]

Becker et al.

[11] 4,232,318

[45] Nov. 4, 1980

[54] DUPLEX MICROWAVE RADIO COMMUNICATION SYSTEM

[75] Inventors: Friedbert Becker, Munich; Gunter Biethan, Neuried; Peter Kloeber, Munich, all of Fed. Rep. of Germany

[73] Assignee: Siemens Aktiengesellschaft, Berlin and Munich, Fed. Rep. of Germany

[21] Appl. No.: 947,052

[22] Filed: Sep. 29, 1978

[30] Foreign Application Priority Data

Sep. 30, 1977 [DE] Fed. Rep. of Germany ....... 2744110
Sep. 30, 1977 [DE] Fed. Rep. of Germany ....... 2744127

[51] Int. Cl.² .............................................. H04L 5/14
[52] U.S. Cl. ....................................... 370/29; 340/48; 375/5; 370/31
[58] Field of Search .................. 343/175, 178; 340/47, 340/48; 333/1.1, 10; 178/58 A

[56] References Cited

U.S. PATENT DOCUMENTS

| | | | |
|---|---|---|---|
| 4,038,653 | 7/1977 | Brewster | 340/47 |
| 4,109,202 | 8/1978 | Kudsia | 333/1.1 |
| 4,115,708 | 9/1978 | Liu | 333/1.1 |

Primary Examiner—David L. Stewart
Attorney, Agent, or Firm—Hill, Van Santen, Steadman, Chiara & Simpson

[57] ABSTRACT

A duplex microwave radio communication and telemetry system for transmitting analog and digital data between fixed stations as well as to mobile stations wherein the microwave oscillator is stabilized by utilizing a free running oscillator which is controlled in frequency with the incoming modulation input and the output of the free running oscillator is supplied to a phase comparator and to a multiplier and the multiplier supplies an output to a mixer which also receives a portion of the input from the microwave oscillator and supplies an input to the phase comparator to provide a control signal for controlling the frequency of the microwave oscillator.

7 Claims, 5 Drawing Figures

DUPLEX MICROWAVE RADIO COMMUNICATION SYSTEM

BACKGROUND OF THE INVENTION

1. Field of the Invention

The invention relates in general to duplex microwave radio communication system for transmission of analog and digital data between mobile transmitter and receiver stations along the side of prescribed routes wherein fixed transmitter receiver stations are located and wherein the transmitter and receiver stations are effective to transmit and receive information in both directions and in which the stations for one route are connected to a central transmitter-receiver station and further the invention relates to a method for stabilizing the microwave oscillator in the transmitter branch of a transmitter-receiver station.

2. Description of the Prior Art

Radio systems of the duplex microwave radio type are important in railroad traffic. For the economic utilization of existing railroad networks which have high density of trains travelling at high speed requires that more efficient and increasing data and signal exchange exist between the trains and the stationary fixed equipment.

The publication "Electric Railways" 44 (1973) Volume 4, at pages 83 through 92 disclose information exchange utilizing a so-called line conductor system. In these systems, inductive wire loops are arranged in the track area for a line conductor system and the wire loops serve as transmitter-receiver antenna for the stationary stations. The transmission of information between the mobile transmitter-receiver stations on the vehicle and these stationary stations utilizes a frequency shift in the frequency range of about 50 kHz and the maximum transmission rate is limited to approximately 1200 bauds. In addition to having limited rate of information flow, the line conductor system has the great disadvantage in that the wire loops particularly during railroad track construction work can be easily damaged which degrades the system.

The disadvantage of mechanical damage in such radio systems can be prevented if the inductive loops for the transmission are abandoned and the stations in contact with one another exchange information by way of radio. Such systems, for example, are disclosed in the publication "ETR" (Railway Technical Review), Volume 10, October 1971 at pages 402 through 411.

In an earlier patent application of the assignee, a radio station is improved utilizing these known systems and it was suggested that the route segments between consecutive stations representing main stations can be subdivided by intermediate stations with the main stations and the intermediate stations which are closest together in distance are combined into transmission segments and the intermediate stations together with the corresponding main stations are utilized for signal and communication exchange with the mobile stations.

SUMMARY OF THE INVENTION

Very high requirements exist for the frequency stability of microwave oscillator in railroad communication sytems which results in the requirement of an economic utilization of the frequency band and also that the IF (Intermediate Frequency) filter arrangements at the receiver utilize efficiently the IF band width available.

Th principal objective of the present invention is to provide a resolution of the problems for a duplex microwave radio system with a technically simple and a relatively inexpensive installation of the transmitter-receiver system in both the stationary and mobile stations. The stabilization of the microwave oscillator in the transmitter of the receiver-transmitter system is accomplished in a simple manner.

A feature of the invention lies in the fact that the mobile and/or the stationary intermediate stations have a transmitter having a modulation input and the transmitter and receiver utilize a joint microwave oscillator and the receiver uses a microwave mixer that includes a demodulator and receives an input from the circulator of an output of the transmitter. The transmitter and receiver branch are connected to a circulator which has a third arm to which a three dB coupler is connected and the third arm lies between the first arm that is connected to the transmitter branch and the second arm which is connected to the receiver branch. Two antennas displaced by 180° in their radiation direction are connected to the three dB coupler. A stabilization circuit for the microwave oscillator is provided in the transmitter and a portion of the output of the microwave oscillator decreased by the decoupling attenuation of the circulator is supplied to the microwave mixer in the receiver and translated to an intermediate frequency when mixed with the received signal and the intermediate frequency is supplied to an amplifier and demodulator which are furnished to the main station by way of a signal cable.

In one advantageous embodiment of the invention, digital modulation transmitted in a cable controls a frequency stable reference source shiftable in frequency for the microwave oscillator such that the oscillator changes in the pulse of the modulation signal between two discrete highly stable frequency conditions during transmission and has a third discrete frequency condition during reception. For semi-duplex operation, the transmission and reception cases alternate in a definite sequence. In full duplex operation, in other words, with simultaneous transmission and reception undesirable intermodulation frequencies which form in the receiver due to the transmitter modulation are eliminated in the IF selectivity, as for example, by the use of electronic switches which are controlled by the binary modulation signals of the transmitter. The switches may be operated with a filter bank connected in series with them and before them or an auxiliary oscillator and an additional mixer in the receiver may be utilized.

Stabilization of the microwave oscillator is accomplished with the FM or FSK modulated signal which is compared with the signal of a free running oscillator which is tunable and has a higher frequency and wherein the free running oscillator is adjusted utlizing an automatic volume control potential. The stabilized output signal of the free running oscillator is multiplied in frequency and supplied to a harmonic mixer which also receives a portion of the output of the microwave oscillator that is to be stabilized. The intermediate frequency formed at the output in the harmonic mixer is compared with the frequency of the free running oscillator in a second phase comparator circuit and the microwave oscillator is adjusted with the output of the second phase comparator circuit.

The FM or a FSK modulation of the reference produced by an oscillator can proceed in the respective intermediate station or the quartz stabilized reference signal for the intermediate stations of a modulation component can be produced in the main station and can be transmitted to the intermediate stations with the FM or FSK modulation, respectively.

Other features, objects and advantages of the invention will be readily apparent from the following description of certain preferred embodiments thereof taken in conjunction with the accompanying drawings although variations and modifications may be effected without departing from the spirit and scope of the novel concepts of the disclosure and in which:

DESCRIPTION OF THE PREFERRED EMBODIMENTS

Figure 1:
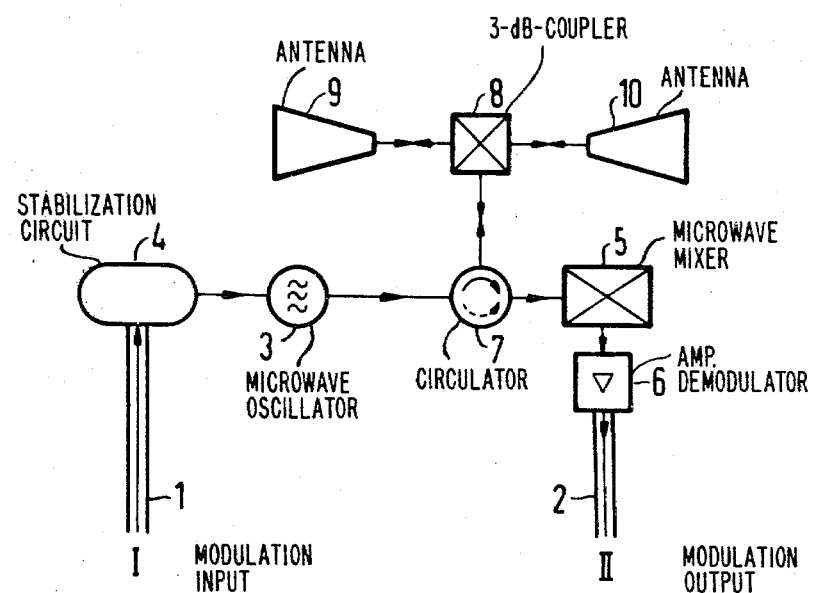
FIG. 1 is a block diagram of the transmitter-receiver arrangement of a relay or mobile station.

FIG. 1 illustrates the transmitter-receiver arrangement of a relay or mobile station in block diagram form. The transmitter-receiver system receives a modulation input I which is supplied to the transmitter and produces an output modulation signal II at the receiver. The input and output modulations are transmitted by signal cables 1 and 2 to a relay station or another mobile station. The transmitter includes a microwave oscillator 3 and a stabilization circuit connected to the oscillator which will be described in greater detail hereafter. The receiver includes a microwave mixer 5 (receiver mixer) which supplies an output to an amplifier demodulator 6. The microwave mixer 5 receives incoming signals from the circulator 7 and also a feed-through mixing signal from the microwave oscillator 3. The transmitter and receiver are connected by the circulator 7 with the microwave oscillator supplying an input to a first leg of the circulator 7. A second leg of the circulator is connected to a 3 dB coupler 8 which divides the incoming and outcoming signals into half and supplies them to oppositely directed antennas 9 and 10 as shown. A third leg is connected to the microwave receiver mixer 5. Most of the energy from the microwave oscillator 3 passes to the antennas 9 and 10 through the second leg of the circulator 7, but a small portion passes as shown in the dashed arrow to the microwave mixer 5 where it is used as a local mixing frequency. Most of the signal from the antennas 9 and 10 pass through the circulator 8 and to the receiver microwave mixer 5.

The feed-through signal from the microwave oscillator 3 which reaches the microwave mixer 5 as shown by the dashed arrow in the circulator 7 converts the received incoming signal from the antennas 9 and 10 into an IF signal of a lower frequency and, thus, the microwave oscillator 3 serves as the local receiver oscillator. The output of the microwave mixer 5 after corresponding processing is converted into digital signals in a FSK demodulator and the digital signals are transmitted to the main station by way of the modulation cable.

The undesirable intermodulation frequencies formed in the receiver during full duplex operation can be eliminated by suitable measures in the IF evaluation system, for example, by using electronic switches controlled by the modulation signals of the transmitters with the switches connected in series with band pass filters. Alternatively, the undesirable modulation components can be eliminated with the use of an auxiliary oscillator in an additional mixer in the receiver.

It is possible that undesirable radiation of the transmitter output during reception occurs from the local oscillator frequency when a single oscillator is used for transmission and reception in semi-duplex operation. By utilizing a third frequency arrangement, for example, in the center of the frequency deviation which condition can be utilized by a non-transmitting stations will cause the undesirable intermediate frequencies to be capable of being removed by means of corresponding IF filtering.

Figure 2:
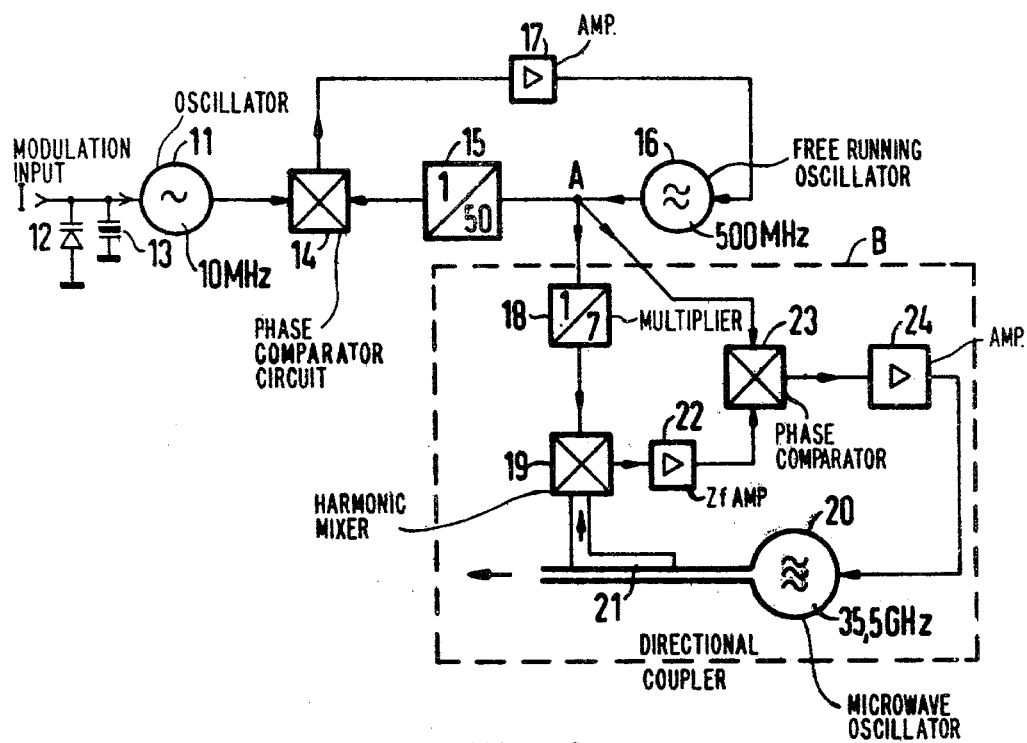
FIG. 2 illustrates a stabilization circuit for the microwave oscillator of a transmitter-receiver arrangement.

FIG. 2 illustrates a stabilization circuit for a transmitter and in which the modulation input is indicated by I. An oscillator 11 which might be tuned to oscillate at a frequency, for example, of f=10 MHz is FM or FSK modulated by means of detuning the resonance of a quartz crystal 13 connected in parallel with a varactor diode 12 between the input I and ground. The modulated signal is supplied to a phase comparator circuit 14 at the output of the oscillator 11 and compared therein with a signal from the free running oscillator 16 (VCO) which may be oscillating at 500 MHz and supplies an input to the phase comparator circuit 14 through a divider 15 which divides its input by a factor of 50 so as to convert the 500 MHz signal from the oscillator 16 to 10 MHz. The phase comparator 14 compares the two inputs and produces an output signal which is supplied to an amplifier stabilization circuit 17 and then to the frequency control input of the free-running oscillator 16 so as to adjust the output of the oscillator 16. A multiplier 18 also receives an output from the free-running oscillator 16 and multiplies its frequency by a factor of 7 and supplies an output to the harmonic mixer 19. In addition, a portion of the signal from the microwave oscillator 20 which is to be stabilized and might, for example, have a frequency f=35.5 GHz is supplied as a local oscillator signal to the harmonic mixer 19 through the directional coupler 21. The intermediate frequency of approximately 500 MHz formed in the harmonic mixer 19 is supplied to an IF amplifier 22 where it is amplified and then supplied as an output to a second phase comparator 23 which compares the output of the amplifier 22 with the output of the 500 MHz oscillator 16 and the output of the phase comparator 23 is supplied to a DC amplifier which supplies an output to the microwave oscillator 20 to control its frequency.

Figure 3:
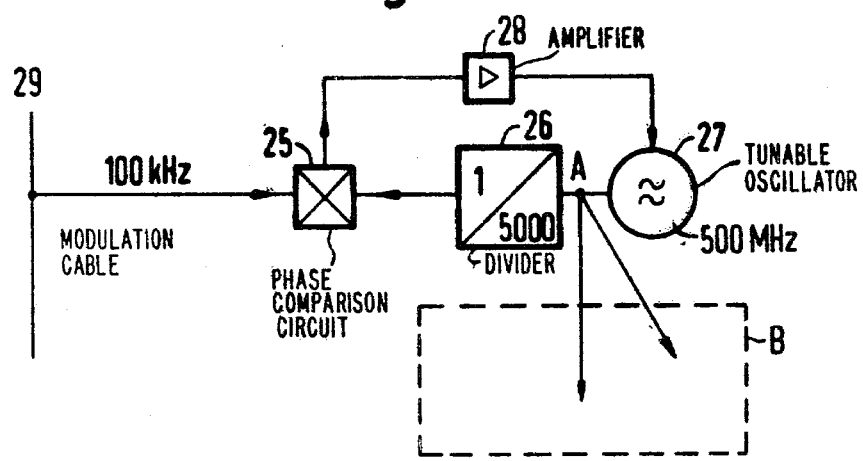
FIG. 3 illustrates a modified version in block diagram form of a stabilization circuit for the microwave oscillator of a transmitter-receiver system.

FIG. 3 illustrates in partial view an additional embodiment of the stabilization circuit which is different from the embodiment illustrated in FIG. 2 and wherein the reference signal having thereon FM or FSK modulation is transmitted to the relay station by way of the signal cable 29 where it is supplied to a phase comparison circuit 25. The incoming signal at 100 kHz is compared in the phase comparator circuit 25 with the output of the free-running tunable 500 MHz oscillator 27 after it has been divided in a divider 26 by a factor of 5000. The output of the phase comparator circuit 25 is supplied to an amplifier 28 which supplies its output to the frequency control of the free-running oscillator 27 to stabilize its frequency.

The additional elements of the modified stabilization circuit illustrated in FIG. 3 is supplied from point A to a circuit B which is shown in dashed line and the circuit B is the same in FIG. 3 as illustrated in FIG. 2. Thus, the additional components illustrated in block B would be the same in FIG. 3 as in FIG. 2.

Figure 4:
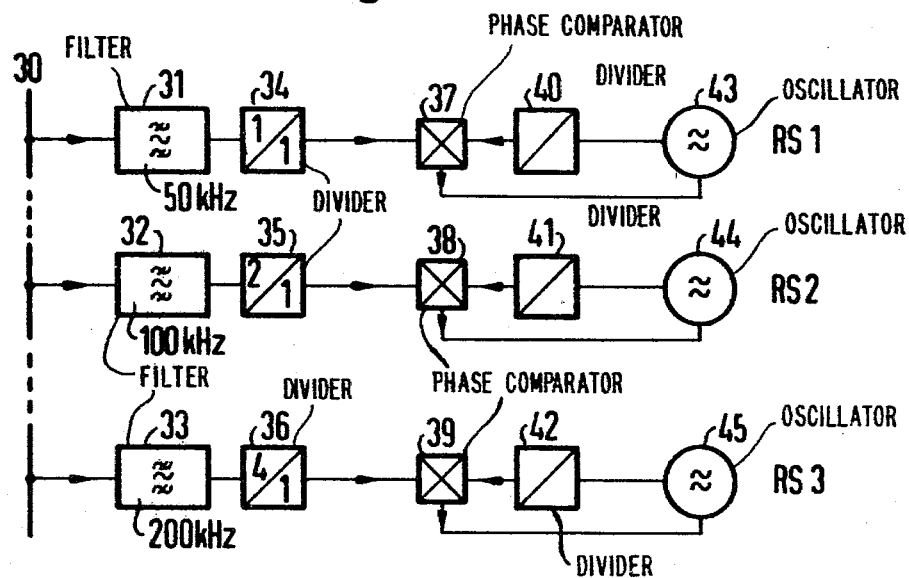
FIG. 4 is a block diagram illustrating a circuit for the distribution of modulation frequencies to relay stations.

If frequency displacement of several relay stations is to be accomplished by staggering the corresponding number of modulation frequencies are transmitted and filtered out by corresponding filters for the respective relay stations. FIG. 4 illustrates a circuit for this purpose. The modulation frequencies for the three relay stations RS1, RS2, RS3 are transmitted by way of a signal cable 30. Each of the relay stations RS1, RS2 and RS3 contain in its input branch filters 31, 32, 33 which receive the input from the cable 30 and are respectively tuned to frequencies of 50 kHz, 100 kHz and 200 kHz, respectively. The output of the filter 31 is supplied to a divider 34 which divides by a factor of 1 and supplies an output at 50 kHz to a phase comparator 37. The phase comparator 37 receives an output from the 500 MHz free-running oscillator 43 through the divider 40 which divides the output of the oscillator 43 to 50 kHz. The output of the phase comparator 37 is supplied to the frequency control input of the oscillator 43. A divider 35 receives the output of the filter 32 which has a pass band of 100 kHz and divides it by 2 to produce a frequency of 50 kHz at the output of the divider 35 and supplies this to a phase comparator 38 which receives an output of the 500 MHz free-running oscillator 44 through the divider 41 which has a dividing factor so as to divide its input down to b 50 kHz. The phase comparator 38 supplies a frequency control output to the oscillator 44 as shown.

The filter 33 has a pass band of 200 kHz and supplies an output to the divider 36 which divides by a factor of 4 and supplies an output at 50 kHz to the phase comparator 39. The oscillator 45 which oscillates at the frequency of 500 MHz supplies an output to the divider 42 which divides its input frequency so as to produce an output at 50 kHz. The phase comparator 39 supplies an output signal to the frequency control input of the oscillator 45 as shown.

Figure 5:
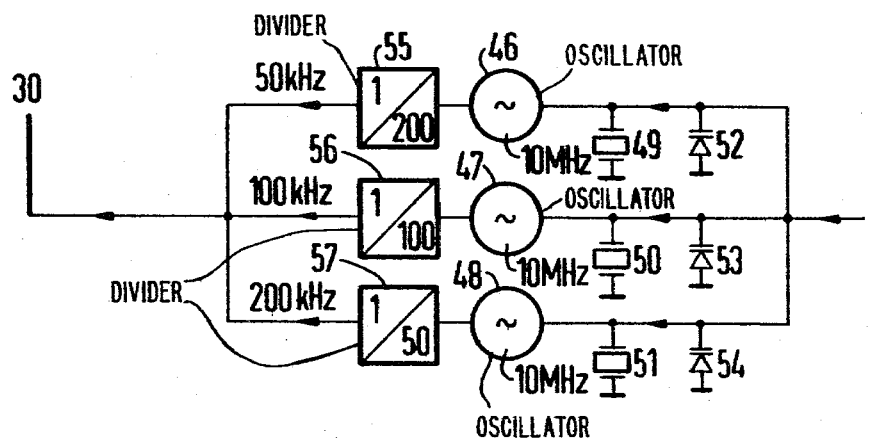
FIG. 5 is a block diagram illustrating quartz crystal oscillators in the main station which produces three different frequencies.

FIG. 5 illustrates quartz generator circuits in the main station which produce at least three different frequencies. In the illustrated example, there are three branches each containing a quartz crystal oscillators 46, 47 and 48 which produce output frequencies at 10 MHz. Oscillator 46 is controlled by crystal 49 and varactor diode 52 connected in parallel between ground and the oscillator 46. Crystal 50 and varactor 53 are connected to the oscillator 47. Crystal 51 and varactor 54 are connected to oscillator 48. The output of oscillator 46 is connected to a divider 55 which divides the output of the oscillator 46 by a factor of 200 to produce a 50 kHz output which is supplied to cable 30. The output of oscillator 47 is supplied to a divider 56 which divides the output of the oscillator 47 by 100 to produce an output of 100 kHz which is supplied to cable 30. The output of oscillator 48 is supplied to divider 57 which divides the output of the oscillator 48 by 50 to produce an output signal of 200 kHz which is supplied to cable 30. The three output signals at frequencies of 50 kHz, 100 kHz and 200 khz are transmitted to the individual relay stations by means of a joint modulation cable 30 where they are processed therein as, for example, as illustrated in FIG. 4. It is to be realized, of course, that the relay stations having different frequencies can also receive different modulated signals.

Although the invention has been described with respect to preferred embodiments, it is not to be so limited as changes and modifications may be made therein which are within the full intended scope as defined by the appended claims.

We claim as our invention:

1. A duplex microwave radio system for the transmission of analog and digital data between movable transmitting and receiving stations which move along pregiven link paths and fixed transmitting and receiver stations which are arranged along these paths at known spacings and which are active for transmitting and receiving in both directions so that the stations of a link path are in communication with a central transmitting receiving station, characterized in that at least one of the movable or fixed stations has a transmitting branch with a modulation input (I) and with a microwave oscillator (3) which is used in common for the transmitting and receiving branches, a stabilization circuit (4) for said microwave oscillator and a microwave mixer (5), an amplifier and demodulator (6) in the receiving branch and a modulation output (II) produced by said receiving branch, characterized in that transmitting and receiving branches are coupled together with a circulator (7) having three arms, one of the arms connected to the transmitting branch and a second one of the arms connected to the receiving branch, a 3-dB-coupler (8) connected to the third one of said arms, two antennae which are displaced in radiation direction by 180° are connected to said 3-dB-coupler (8), and in addition to the received signal, a signal from the microwave oscillator (3), which is decreased by the decoupling attenuation of the circulator (7), is fed to said microwave mixer in the receiving branch to serve as a local oscillator signal and the output of said mixer supplied to said amplifier and demodulator and the output of said amplifier-demodulator connected to a master station with a signal cable.

2. A microwave radio system according to claim 1, wherein digital modulation transmitted by cable controls a stable frequency reference source which can be shifted in frequency to control the microwave oscillator such that said microwave oscillator during transmission varies at the pulse frequency of the modulation signal between two discrete highly stable frequency conditions, and during reception assumes a third discrete frequency condition.

3. A microwave radio system according to claim 2, characterized in that transmission and reception conditions alternate in a definite sequence for semi-duplex operation.

4. A microwave radio system according to claim 2, characterized in that undesirable intermodulation frequencies, formed in the receiver by the transmitter modulation during full duplex operation are eliminated in the IF evaluation by means of electronic switches controlled by the binary modulation signals of the transmitter, said switches connected in series and a filter bank, an auxiliary oscillator and an additional mixer in the receiver branch which eliminates said intermodulation frequencies.

5. A method for the stabilizing the microwave oscillator in the transmitting branch of a transmitting receiving device for a duplex microwave radio system using FM or FSK modulation characterized in that the modulated signal comprising the reference signal for the microwave oscillator is compared in a first phase comparison circuit (14) with the signal of a free running detunable oscillator (16) having a higher frequency, and which signal is divided in a frequency divider (15) by a dividing factor, and said oscillator is readjusted with a regulating voltage comprising, the steps of multiplying the stabilized signal output of the free running oscillator (16) in a frequency multiplier (18), supplying the output of multiplier (18) to a harmonic wave mixer (19), to which at the same time a portion of the output signal of the microwave oscillator (20) which is to be stabilized is supplied, comparing in a second phase comparison circuit (13) the intermediate frequency output signal from the mixer (19) with the stabilized output frequency of the free running oscillator (16), and readjusting the frequency of the microwave oscillator (20) with the output voltage of said second phase comparison circuit (23).

6. A method according to claim 5, characterized in that the FM or FSK modulation of a reference signal produced by a local oscillator is utilized in an intermediate station.

7. A method according to claim 5, characterized in that the quartz stabilized reference signal for intermediate stations is produced in the main station and is transmitted to the intermediate station using FM or FSK modulation.

* * * * *